United States Patent
Zeldis et al.

(10) Patent No.: US 7,115,631 B2
(45) Date of Patent: *Oct. 3, 2006

(54) METHODS FOR TREATMENT OF COGNITIVE AND MENOPAUSAL DISORDERS WITH D-THREO METHYLPHENIDATE

(75) Inventors: Jerome B Zeldis, Princeton, NJ (US); Herbert J. Faleck, West Orange, NJ (US); Vikram Khetani, Short Hills, NJ (US); Andrew L. Zeitlin, Basking Ridge, NJ (US); Maghsoud M. Dariani, Fanwood, NJ (US); David Sterling, Branchburg, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/195,974

(22) Filed: Jul. 16, 2002

(65) Prior Publication Data

US 2002/0198234 A1 Dec. 26, 2002

Related U.S. Application Data

(63) Continuation-in-part of application No. 09/903,803, filed on Jul. 12, 2001, now Pat. No. 6,486,177.

(51) Int. Cl.
*A61K 31/445* (2006.01)

(52) U.S. Cl. .................................................. 514/317
(58) Field of Classification Search ............... 514/315, 514/317
See application file for complete search history.

(56) References Cited

U.S. PATENT DOCUMENTS

| | | | | |
|---|---|---|---|---|
| 2,507,631 | A | 5/1950 | Hartman et al. | 260/294 |
| 2,957,880 | A | 10/1960 | Rometsch | 546/233 |
| 4,137,300 | A | 1/1979 | Sheth et al. | 424/460 |
| 4,992,445 | A | 2/1991 | Lawter et al. | 514/279 |
| 5,104,899 | A | 4/1992 | Young et al. | 514/646 |
| 5,114,946 | A | 5/1992 | Lawter et al. | 514/279 |
| 5,217,718 | A | 6/1993 | Colley et al. | 424/449 |
| 5,283,193 | A | 2/1994 | Yamamoto et al. | 435/280 |
| 5,284,769 | A | 2/1994 | Evans et al. | 435/280 |
| 5,331,000 | A | 7/1994 | Young et al. | 514/570 |
| 5,362,755 | A | 11/1994 | Barberich et al. | 514/649 |
| 5,375,693 | A | 12/1994 | Woosley et al. | 514/317 |
| 5,449,743 | A | 9/1995 | Kobayashi et al. | 528/355 |
| 5,733,756 | A | 3/1998 | Zeitlin et al. | 435/122 |
| 5,773,478 | A | 6/1998 | Richards et al. | 514/649 |
| 5,837,284 | A | 11/1998 | Mehta et al. | 424/459 |
| 5,874,090 | A | 2/1999 | Baker et al. | 424/600 |
| 5,908,850 | A | 6/1999 | Zeitlin et al. | 514/315 |
| 6,031,124 | A | 2/2000 | Fox et al. | 560/37 |
| 6,113,879 | A | 9/2000 | Richards et al. | 424/9.1 |
| 6,127,385 | A | 10/2000 | Midha et al. | 514/317 |
| 6,221,883 | B1 | 4/2001 | Baldessarini et al. | 514/317 |
| 6,242,464 | B1 | 6/2001 | Harris et al. | 514/317 |
| 6,344,215 | B1 | 2/2002 | Bettman et al. | 424/459 |
| 6,355,656 | B1 * | 3/2002 | Zeitlin et al. | 514/317 |
| 6,395,752 | B1 | 5/2002 | Midha et al. | 514/317 |
| 6,441,178 | B1 | 8/2002 | Zavareh et al. | 546/238 |
| 6,468,504 | B1 | 10/2002 | Richards et al. | 424/9.1 |
| 6,486,177 | B1 * | 11/2002 | Zeldis et al. | 514/317 |
| 6,531,489 | B1 | 3/2003 | Harris et al. | 514/317 |
| 2002/0019535 | A1 | 2/2002 | Zavareh et al. | 546/227 |
| 2002/0032335 | A1 | 3/2002 | Langston et al. | 546/238 |
| 2003/0049205 | A1 | 3/2003 | Richards et al. | 424/9.1 |
| 2003/0105134 | A1 | 6/2003 | Harris et al. | 514/317 |

FOREIGN PATENT DOCUMENTS

| | | |
|---|---|---|
| CA | 2 376 215 A1 | 12/2001 |
| CA | 2 223 643 C | 12/2003 |
| EP | 0 885 191 B1 | 1/2002 |
| EP | 0 889 874 B1 | 1/2002 |
| EP | 0 841 928 B1 | 9/2002 |
| EP | 0 879 228 B1 | 10/2002 |
| EP | 0 958 281 B1 | 3/2004 |
| GB | 589625 | 1/1945 |
| GB | 788226 | 12/1957 |
| GB | 878167 | 9/1961 |
| RU | 466229 | 4/1975 |
| WO | 96/41617 A1 | 12/1996 |
| WO | WO 97/03671 | 2/1997 |
| WO | WO 97/03672 | 2/1997 |
| WO | WO 97/03673 | 2/1997 |
| WO | WO 97/27176 | 7/1997 |
| WO | WO 97/28124 | 8/1997 |
| WO | WO 97/32851 | 9/1997 |
| WO | WO 97/35836 | 10/1997 |
| WO | WO 98/23263 | 6/1998 |
| WO | WO 98/25902 | 6/1998 |
| WO | WO 98/31668 | 7/1998 |
| WO | WO 00/74680 A1 | 12/2000 |
| WO | WO 01/43730 A3 | 6/2001 |

OTHER PUBLICATIONS

Angrist, et al., *J. Clinical Psychopharmacology*, 1992, 12(4), 268–272.
Barkley, et al, *Pediatrics*, 1990, 86(2), 184–192.
Barkley, et al., *Pediatrics*, 1991, 87(4), 519–531.
Golinko, *Prog. Neuro–Psychopharmacol & Biol. Psychiat.*, 1984, 8, 1–8.

(Continued)

*Primary Examiner*—Raymond J Henley, III
(74) *Attorney, Agent, or Firm*—Woodcock Washburn, LLP

(57) ABSTRACT

In one aspect, the present invention is directed to methods for treating fatigue, neurobehavioral slowing and other cognitive disorders and defects due to cancers and treatments associated with cancers, and similar conditions. In a further aspect, the present invention is directed to methods for treating disorders related to menopause, including executive function defects. The methods involve the administration of a composition comprising D-threo methylphenidate that is substantially free of L-threo methylphenidate and of erythro forms of methylphenidate.

56 Claims, No Drawings

OTHER PUBLICATIONS

Green, *Pediatric Psychopharmacology,* 1992, 15(1), 1–27.

Holmes, et al., "Psychostimulant response in aids–related complex patients," *J. Clin. Psychiatry,* 1989, 50(1), Biosis Abstract No. 87129969, 1989, 5–8.

Scott, "Stereoisomers and drug toxicity," *Drug Safety,* 1993, 8(2), 149–159.

Srinivas, et al., "Enantioselective pharmacolinetics and pharmacodynamics of racemic threo–methylphendiate in children with attention deficite hyperactivity disorder," *Clin. Pharmacol. Ther.,* Biois Abstract No. 95066168, 1992, 52(5), 561–568.

White, et al., "Methylphenidate as a treatment for depression in acquired immunodeficiency syndrome: an n–of–1 trial," *J. Clin. Psychiatry,* 1992, 53(5), 153–156.

Aoyama, et al., "Pharmacolinetics and pharmacodynamics of (=)–threo–methylphenidate enantiomer in patients with hypersomjnia," *Clin. Pharmacol. Ther.,* 1994, 55(3), 270–276.

Bowden, K., et al., "Reactions of carbonyl compounds in basic solutions, Part 15. The alkaline hydrolysis of N–methyl, N–phenyl, and bicyclo lactams, penicillins, and N–alkyl–n–methylacetamides," *J. Chem. Soc. Perkin Trans.,* 1990, 2(12), 2111–2116.

Brown C., "Pharmacological action and drug development," Chirality in Drug Design and Synthesis, *Academic Press Inc.,* 1990, 4–7.

Brown, G., "The use of methylphenidate for cognitive decline associated with HIV disease," *Intl. J. Psych. Med.,* 1995, 25(1), 21–37.

Corey, et al., "A new synthetic approach to the penicillins," *J. Amer. Chem. Soc.,* 1965, 87(11), 2518–2519.

Ding, L.K., et al., "Cis– and trans–azetidin–2–ones from nitrones and copper acetylide," *J. Chem. Soc. Perkin I,* 1976, 22, 2382–2386.

Douzenis, et al., Phychiatric disorder in HIV disease: description of 200 referrals to a liaison psychiatry service, *Proc. 7th Int'l conf. AIDS,* 1991, 1, 2135–2215.

Earle, et al., "Synthesis and hydrolysis of some fused–ring β–lactams," *J. Chem. Soc.,* 1969, 2092098.

Greehill, "Pharmacologic treatment of attention deficit hyperactivity disorder," *Pediatric Psychoparmacology,* 1992, 15(1), 1–27.

Greenhill, L., "Attention–deficit hyperactivity disorder child & adol.," *Psych. Clin. N.A.,* 1995, 4, 123–165.

Hou, J.P., et al., "Beta–lactam antibiotics: their physicochemical properties and biological activities in relation to structure," *J. Pharm. Sci.,* 1971, 60(4), 503–532.

Klibanov, A.M. "Asymmetric transformations catalyzed by enzyumes in organic solvents," *Acc. Chem. Res.,* 1990, 23, 114–120.

Moll, F., "Darstellung von 1–Asa–bicyclo [4.2.0] octan–2–on," *Naturforsch Teil B.,* 1966, 21, 297.

Navia, et al., "The AIDS dementia complex: I. Clinical features," *Annals of Neurology,* 1986, 19, 517–524.

Patrick, et al., "Pharmacology of the enantiomers of threo–methylphenidate," *J. Pharmacol. & Exp. Terhap.,* 1987, 241, 152–158.

Rieder, et al., "Diagnosis of sulfonamide hypersensitivity reactions by in–vitro "rechallenge" with hydroxylamine metabolites," *Ann. Intern. Med.,* 1989, 110, 286–289.

Srinivas, et al., "Enantiomeric gas chromatography assay with electron capture detection for d–ritalinic acid in plasma," *J. Chromatagraph,* 1990, 530, 327–336.

Srinivas, et al., "Sterioselective disposition of methylphenidate in children with attention deficit disorder," *J. Pharmacol. Exp. Ther.,* 1987, 241, 300–306.

Srinivas, et al., "Anantioselective pharmacokinetics of dl–threo–methylphenidate in humans," *Pharmacol Res.,* 1993, 10, 14–21.

Staal, et al., "Glutathione deficiency and human immunodeficiency virus infection," *Lancet,* 1992, 339, 909–912.

Uetrecht, et al., "Idiosyncratic drug reactions: possible role of reactive metabolites generated by leukocytes," *Pharmacol Res.,* 1989, 6, 265–273.

"Attention–deficit and disruptive behavior disorders: Attention–deficit/hyperactivity disorder," American Psychiatric Association, Diagnostic and Statistical Manual of Mental Disorders, *Fourth ed. (DSM–IV)* Washington, DC, 1994, 78–85.

Beck, A.T., et al., "Assessment of depression: the depression inventory," *Mod. Probl. Pharmacopsychiatry,* 1974, 7, 155–169.

Brown, T.E., "Attention deficit disorders and comorbidities in children adolescents and adults," *American Psychiatric Press, Washington, DC,* 2000, 40–41.

Bruera, E., et al., "Neuropsychological effects of methylphenidate in patients receiving a contiuous infusion of narcotics for cancer pain," *Pain,* 1992, 48, 163–166.

Cella, D.F., et al., "The functional assessment of cancer therapy scale: development and validation of the general measure," *J. Clin. Oncol.,* 1993, 11(3), 570–579.

Srinivas, N.R., et al., "Enantioselective pharmacokinetics and pharmacodynamics of dl–threo–methylphenidate in children with attention deficit hyperactivity disorder," *Clin. Pharmacol. Ther.,* Nov. 1992, 52, 561–568.

Faust, D., et al., "The development and initial validation of a sensitive bedside cognitive screening test," *J. Nerv. Ment. Dis.,* 1989, 177(1), 25–31.

Folstein, S.E., et al., "Minimental state"; a practical method for grading the cognitive state of patients for the clinician,*J. Psychiatry Res.,* 1975, 12, 189–198.

Kaplan, E.F., et al., The Boston Naming Test, Boston, 1978.

Meyers, C.A., et al., "Methylphenidate therapy improves cognition, mood, and function of brain tumor patients," *J. Clincial Oncology,* Jul. 1998, 16(7), 2522–2527.

Radloff, L.S., "The CES–D scale: a self–report depression scale for research in the general population," *Applied Psychological Measurement,* Summer 1977, 1(3), 385–401.

Reitan, R.M., "Validity of the trail making test as an indicator of organic brain damage," *Perceptual Motor Skills,* 1958, 8, 271–276.

Wechsler D., Wechsler Adult Intelligence Scale–Revised Manual, New York, Psychological Corporation, 1981.

Weitzner, M.A., et al., "The functional assessment of cancer therapy (FACT) scale: development of a brain subscale and revalidation of the general version (FACT–G) in patients with primary brain tumors," *Cancer,* Mar. 1, 1995, 75(5), 1151–1161.

Yee, J.D., et al., "Dextromaphetamine or methylphenidate as adjuvants to opioid analgesia for adolescents with cancer," *J. Pain and Symptom Management,* Feb. 1994, 9(2), 122–125.

Yellin, S.B., et al., "Measuring fatigue and other anemia–related symptoms with the functional assessment of cancer therapy (FACT) measurement system," *J. pain Symptom Manage.,* Feb. 1997, 13(2), 63–74.

Hales, R.E., et al., "Psychopharmacologic issues in the diagnosis and treatment of organic mental disorders," *Psychia. Clinics of North America,* Dec. 1984, 7(4), 817–829.

Brown, T.E., "Emerging understandings of attention–deficit disorders and comorbidities," Attention–Deficit Disorders and Comorbidities in Children, Adolescents, and Adults, *American Psychiatric Press, Inc.,* 2000, Chapter 1, 3–55.

Bruera, E., et al., "Use of methylphenidate as an adjuvant to narcotic analgesics in patients with advanced cancer," *J. Pain and Symptom Management,* Mar. 1989, 4(1), 3–6.

Bruera, E., et al., "Overwhelming fatique in advanced cancer," *Am. J. Nursing, Pain Consult,* Jan. 1988, 99–100.

Bruera, E., et al., "Narcotics plus methylphenidate (ritalin) for advanced cancer pain," *Am. J. Nursing, Pain and Symptom Consult,* Nov. 1988, 1665–1666.

Bruera, E., et al., "The use of methylphenidate in patients with incident cancer pain receiving regular opiates, A preliminary report," *Pain,* ISSN 0304–3959, Jul. 1992, 50(1), 75–77.

Bruera, E., "Methylphenidate associated with narocotics for the treatment of cancer pain," *Cancer Treatment Reports,* Jan. 1987, 71(1), 67–70.

Briera, E., "Neuropsychological effects of methylphenidate in patients receiving a continuous infusion of narcotics for cancer pain," *Pain,* Feb. 1992, ISSN 0304–3959, 48(2), 163–166.

DeLong, R., et al., "Methylphenidate in neuropsychological sequelae of radiotherapy and chemotherapy of childhood brain tumors and leukemia," *J. Child Neurology,* Oct. 1992, 7, 462–463.

Fernandez, F., et al., "Methylphenidate for depressive disorders in cancer patients," *Psychosomatics,* Sep. 1987, 28(9), 455–461.

Fernandez, F., et al., "Methylphenidate treatment for patients with head and neck cancer," *Head and Neck Surgery,* Mar./Apr. 1986, 8(4), 296–300.

Massie, M.J., et al., "Diagnosis and treatment of depression in the cancer patient," *Clinical Psychiatry,* Mar. 1984, vol. 45, 3(2), 25–29.

Macleod, A.D., et al., "Methylphenidate in terminal depression," *J. Pain and Symptom Management,* Sep. 1998, 16(3), 193–198.

Meyers, C.A., et al., "Methylphenidate therapy improves cognition, mood, and function of brain tumor patients," *J. Clinical Oncology,* Jul. 1998, 16(7), 2522–2527.

Nakano, T., et al., Algorithm for the treatment of major depression in patients with advanced cancer, *Psychiatry and Clinical Neurosciences,* Proceedings of the International Meeting on Japanese Psychopharmacology Algorithms Yokohama, Apr. 23, 1998, ISSN1323–1316, 1999, Supplement 53, S61–S65.

Olin, J., et al., "Psychostimulants for depression in hospitalized cancer patients," *Psychosomatics,* Jan.–Feb. 1996, 37(1), 57–62.

O'Neill, W.M., "The cognitive and psychomotor effects of opioid drugs in cancer pain management," *Cancer Surveys,* Palliative Medicine Problem Areas in Pain and Symptom Management, 1994, 21, 67–84.

Plutchik, L., et al., "Methylphenidate in post liver transplant patients," *Psychosomatics,* Mar.–Apr. 1998, 39(2), 119–123.

Reich, M.G., "Amphetamines in oncology: review of the literature," *Cancer,* 1996, 83, 891–900 (English abstract).

Roehrs, T., et al., "Sleepiness and the reinforcing and subjective effects of methylphenidate," *Exp. Clin. Psychopharmacol,* 1999, 7(2), 145–150 (Abstract 1 page).

Stiebel, V., et al., "Long–term methylphenidate use in the medically ill patient with organic mood syndrome," *Psychosomatics,* Fall 1990, 31(4), 454–456.

Vigano, A., et al., "Methylphenidate for the management of somatization in terminal cancer patients," *J. Pain and Symptom Management,* Feb. 1995, 10(2), 167–170.

Weitzner, M.A., et al., "Methylphenidate in the treatment of neurobehavioral slowing associated with cancer and cancer treatment," *J. Neuropsychiatry,* Summer 1995, 7(3), 347–350.

Wilens, T.E., et al., "Pharmacotherapy of attention–deficit/hyperactivity disorder," *Attention–Deficite Disorders with Comorbities, Chapter 16,* 509–535 (no date available).

Yee, J.D., et al., "Dextroamphetamine or methylphenidate as adjuvants to opioid analgesia for adolescents with cancer," *J. Pain and Symptom Management,* Feb. 1994, 9(2), 122–125.

Abwal, H.A., et al., "The Effects of methylphenidate (MP) on narcotic–induced cognitive failure (MICF)," *Am. Soc. Clin. Oncology,* $27^{th}$ Annual Meeting, May 19–21, 1991, 1385, 1992, vol. 11, p. 397.

Portenoy, R.K. (Ed.), "Worth Repeating: Use of methylphenidate as an adjuvant to narcotic analgesics in patients with advanced cancer," *Pharmacology,* year unknown, 2 pages.

Wilwerding, M.B., et al., "A randomized crossover evaluation of methylphenidate in cancer patients receiving strong narcotics," *Am. Soc. Clin. Oncology,* $29^{th}$ Annual Meeting May 16–18, 1993, 1615, 1993, vol. 12, p. 464.

Aoyana, T., et al., Gas chromatographic–mass spectrometric analysis of *threo*–methylphenidate enantiomers in plasma, *J. Chromatography,* 1989, 494, 420–423.

Axten, J.M., et al., "A stereoselective synthesis of dl–threo-methyphenidate: preperation and biological evaluation of novel analogues,"*J. Org. Chem.,* 1998, 63, 9628–9629.

Axten, J.M. et al., "Enantioselective synthesis of D–*threo*–methylphenidate," *J. Am. Chem. Soc.,* 1999, 121, 6511–6512.

Davies, H.M.L., et al., "Highly regio–, diastereo–, and enantioselective C–H insertions of methyl aryldiazoacetates into cyclic N–boc–protected amines, asymmetric synthesis of novel $C_2$–symetric amines and *threo*–methylphenidate," *J. Am. Chem. Soc.,* 1999, 121, 6509–6510.

Deutch, H.M., et al., "Synthesis and pharmacology of potential cocaine antagonists. 2. Structure–activity relationship studies of aromatic ring–substituted methylphenidate analogs," *J. Med. Chem.,* 1996, 39, 1201–1209.

Dirksen, S.J.H., et al., "A postmarking clinical experience study of Metadate® CD," *Curr. Med. Res. and Opinion,* 2002, 18(7), 371–380.

Eckerman, D.A., et al., "Enantioselective behavioral effects of *threo*–methylphenidate in rats," *Pharmac. Biochem. & Behav.,* 1991, 40, 875–880.

Hubbard, J.W., et al., "Enantioselective aspects of the disposition of *dl–threo*–methylphenidate after the administration of a sustained–release formulation to children with attention deficit–hyperactitiy disorder," *J. of Pharmac. Sci.,* 1989, 78(11), 944–947.

Lim, H.K., "Enantiomeric resolution of dl–threo–methylphenidate, U.S.P. (Ritalin®), by high–performance liquid chromatography," *J. of Chromatography*, 1985, 328, 378–386.

Matsumura, Y., et al., "A convenient method for synthesis of enantiomerically enriched methylphenidate from N–methoxycarbonylpiperidine," *Organic Letters*, 1999, 1(2), 175–178.

Naito, T., et al., "Rearrangement of sulfonamide derivatives. V. Syntheses of methyl β–phenyl–2–and 4–piperidineacetate," *Chem. Pharm. Bull.*, 1964, 12(5), 588–590.

Panizzon, Leandro, "Preparation of pyridyl–and piperidylarylacetonitriles and some derivatives.", *Helvetica Chimica Acta*, 1944, 27, 1748–1756.

Prashad, M., et al., "Enzymatic resolution of (±)–threo–m-ethylphenidate," *Tetrahedron: Asymmetry*, 1998, 9, 2133–2136.

Prashad, M., et al., "Enantioselective synthesis of (2S, 2'R)–erythro–methylphenidate," *Tetrahedron: Asymmetry*, 1999, 10, 3479–3482.

Prashad, M., "The first enantioselective synthesis of (2,R,2', R)–threo(+)–methylphenidate hydrochloride," *J. Org. Chem.*, 1999, 64, 1750–1753.

Rochdi, M., et al., "Dose–proportional pharmacokinetics of a methylphenidate extended–release capsule," *Int. J. of Clin. Pharma. And Theraps.*, 2004, 42(5), 285–292.

Thai, D.I., et al., "Asymmetric synthesis and pharmacology of methylphenidate and its para–substituted derivatives," *J. Med. Chem.*, 1998, 41, 591–601.

Panizzon, L., Preparation of pyridyl and piperidyl arylacetonitriles and of a number of conversion products (Part I) *Helvetica Chimica Acta*, 1944, 27, 1748–1756 (translation; previously cited with English abstract).

Medline Abstract No. 11406895 of Sarhill et al., American Journal of Hospice & Palliative Care, (May–Jun. 2001), 18(3), 187–9.*

Biosis Abstract No. 1987:128205 of Bruera et al., Cancer Treatment Reports, (1987), vol. 71, No. 1, pp. 67–70.*

Aoyama, T., et al., "Nonlinear kinetics of threo–methylphenidate encantiomers in a patient with narcolepsy and in healthy volunteers," *Eur. J. Clin. Pharmacol.*, 1993, 44, 79–84.

Barkley, R. A., et al., "The adolescent outcome of hyperactive children diagnosed by research criteria: I. An 8–year prospective follow–up study," *J. Am. Acad. Adolesc. Psychiatry.*, 1990, 29(4), 546–557.

Baughman, Jr., F. A., "Treatment of Attention–Deficit/Hyperactivity Disorder," *JAMA.*, Apr. 28, 1999, 218(16), 1490–1491.

Bruera, E., and Neumann, C. M., "The uses of psychotropics in symptom management in advanced cancer," *Psycho–Oncology.*, 1998, 7, 346–358.

Carey, W. B., "What the multimodal treatment study of children with attention–deficit/hyperactivity disorder did and did not say about the use of methylphenidate for attention deficits," *Pediatrics*, 2000, 863–864.

Coyle, J.T., "Psychotic drug use in very young children," *J. Am. Med. Assn.*, 2000, 283(8), 1059–1060.

Tripp, G. and Alsop, B., "Sensitivity to reward frequency in boys with attention deficit hyperactivity disorder," *J. Clin. Child Psychology.*, Sep. 1999, 28(3), 366–375.

Garland, E. J., "Pharmacotherapy of adolescent attention deficit hyperacitivity disorder: challenges, choices and caveats," *J. Psychopharmacology.*, 1998, 12(4), 385–395.

Golden, G. S.., "Role of attention deficit hyperactivity disorder in learning disabilities," *Seminars in Neurology.*, 1991, 11(1), 35–41.

Goldman, L. S., et al., "Diagnosis and treatment of attention–deficit/hyperactivity disorder in children and adolescents," *J. Am. Med. Assn.*, 1998, 279(14), 1100–1107.

Jadad, A. R., et al., "Review: Pharmacologic interventions are more effective than non–pharmacologic for attention–deficit hyperactivity disorder," *Therapeutics, ACP Journal Club.*, Nov./Dec. 2000, 110.

Jensen, P. S., et al., "Are stimulants over–prescribed? Treatment of ADHD in four U.S. communities," *J. Am. Acad. Child Adolesc. Psychiatry.*, Jul. 1999, 37(7), 797–804.

Kimko, H. C., et al., "Pharmacokinetics and Clinical effectiveness of methylphenidate," *Clin. Pharmacokinetics.*, Dec. 1999, 37(6),1 457–470.

LeFever, G. B., et al., "The extent of drug therapy for attention deficit–hyperactivity disorder among children in public schools," *American Journal of Public Health*, (Sep., 1999), (89)9, 1359–1364.

Lin, J. H., and Lu, A. H., "Role of pharmacolinetics and Metabolism in drug discovery and development," *Pharmacological Reviews*, 1997, 49(4), 403–449.

Llana, M. E. and Crismon, M. L., "Methylphenidate: increased abuse or appropriate use?, " *J. Amer. Pharmaceut. Assn.*, Jul.–Aug. 1999, 39(4), 526–530.

MacDougall, M. K., et al., "Symptom control in the pregnant cancer patient," *Seminars in Oncology.*, 2000, 27(6), 704–711.

McCarthy, M., "USA to improve care of children with ADHA," *The Lancet*, 2000, 355, 1161.

Mehta, M. A., et al., "Methylphenidate enchances working memory by modulating discrete frontal and parietal lobe regions in the human brain," *J. Neurosci.*, 2000, 20RC65: (1–6).

No author, "*Methylphenidate hydrochloride*," Environmental Health Perspectives, 1997, 105 (supp 1), 319.

Schweitzer J. B., et al., "Attention deficit hyperactivity disorder," *Adv. Pathophysiol. And Treat. Psychiatric Disorders: Implications for Internal Med.*, 2001, 85(3), 757–777.

Spencer, T., et al., "Pharmacotherapy of attention–deficit hyperactivity disorder across the life cycle," *J. Am. Acad. Adolesc. Psychiatry.*, 1996, 35(4), 409–432.

Stein, M. A.., et al, "Methylphenidate dosing: Twice daily versus three times daily," *Pediatrics.*, 1996, 98(4), 748–756.

Swanson, J. M., et al., "Acute tolerance to methylphenidate in the treatment of attention deficit hyperactivity disorder in children," *Clin. Pharmacology and Therapeu..*, Sep. 1999, 66(3), 295–305.

Swanson, J. M., et al., "Analog classroom assessment of Adderall in children with ADHA," *J. Am. Acad. Adolesc. Psychiatry.*, 1998, 37(5), 519–525.

Taylor, M. A., "Attention–deficit hyperactivity disorder on the frontlines: Management in the primary care office," *Comp. Ther.*, Jun.–Jul. 1999, 25(6/7), 313–325.

Ward, M. F., et al., "The Wender Utah rating scale: an aid in the retrospective diagnosis of childhood attention deficit hyperactivity disorder," *Am. J. Psychiatry.*, 1993, 150(6), 885–890.

Weiler, M. D., et al., "Mother and Teacher Reports of ADHD Symptoms: DSM–IV Questionnaire Data," *J. Am. Acad. Child Adolesc. Psychiatry*, Sep. 1999, 38(9), 1139–1147.

Zametkin, A. J. and Ernst, M., "Problems in the management of attention–deficit/hyperactivity disorder," *New. Eng. Jour. Med.*, Jan. 1999, 340(1), 40–46.

Zito, J. M., et al., "Trends in the prescribing of psychotropic medications to preschoolers," *J. Am. Med. Assn.*, 2000, 283(8), 1025–1030.

Aoyama, T. et al., "Pharmacodynamic Modeling for Change of Locomotor Activity by Methyllphenidate in Rats," *Pharmaceutical Research*, 1997, 14(11), 1601–1606.

Aoyama, T. et al., "Pharmacokinetics and pharmacodynamics of methylphenidate enantiomers in rats," *Psychopharmacology*, 1996, 127, 117–122.

Challman, T.D., et al., "Methylphenidate: its pharmacology and uses," *Mayo Clin Proc.*, 2000, 75, 711–721.

Davids, E. et al., "Stereoselective effects of methylphenidate on motor hyperacitivity in juvenile rats induced by neonatal 6–hydroxydopamine lesioning," *Psychopharmacology*, 2002, 160, 92–98.

Ding, Y.–S. et al., "Chiral drugs: comparison of the pharmacokinetics of [11 C]d–threo and *l–threo*–methylphenidate in the human and baboon brain," *Psychopharmacology*, 1997, 131, 71–78.

Ding, Y.–D. et al., "Is the L–Threo Enantiomer of Methylphenidate (Ritalin) Inactive in the Brain when the Drug is Given Orally?" *ACNP 41$^{st}$ Annual Meeting*, Dec. 8–12, 2002, Scientific Abstract No. 119.

Ding, Y–S. et al., "Brain Kinetics of Methylphenidate (Ritalin) Enantiomers After Oral Administration," *Synapse*, Sep. 2004, 53, 168–175.

Jonkman, L.M. et al., "Differences in plasma concentrations of the D–and L–threo methylphenidate enantiomers in responding and non–responding children with attention–deficit hyperactivity disorder," *Psychiatry Research*, 1998, 78, 115–118.

Modi, N. B. et al., "Dose–Proportional and Sterospecific Pharmacokinetics of Methylphenidate Delivered Using an Osmotic, Controlled–Release Oral Delivery System,"*J Clin Pharmacol*, 2000, 40, 1141–1149.

Patrick K S et al: "The Absorption Of Sustained–Release Methylphenidate Formulations Compared To An Immediate–Release Formulation" *Biopharmaceutics And Drug Disposition*, 1989, Wiley, Chichester, US, 10(2), 165–171.

Patrick, K. S. et al., "New methylophenidate formulations for the treatment of attention–deficit/hyperacitivity disorder," *Expert Opin. Drug Deliv.*, 2005, 2(1), 121–143.

Patrick, K.S. et al., "Pharmacology of Methylphenidate, Amphetamine Enantiomers and Pemoline in Attention–Deficit Hyperactivity Disorder," *Human Psychopharmacology*, 1997, 12, 527–546.

Patrick, K.S. et al, "Synthesis, Pharmacology and Human Metabolic Formation of Ethylphenidate: the Transesterification Product of Methylphenidate and Ethanol," *The 56$^{th}$ Southeast Regional Meeting 2004*, Nov. 10–13, 2004 1 page.

Quinn, D. M. P., "Methylphenidate: The Role of the d–Isomer," undated, Department of Psychiatry, College of Medicine, University of Saskatchewan, Saskatoon, Saskatchewan, Canada, 369–373.

Rouhi, R. I. et al., "Chirality at work," *C&EN*, May 5, 2003, 56–61.

Shader R. I. et al. "Population pharmacokinetics of Methylphenidate in Children with Attention–Deficit Hyperacitivity Disorder,"*J. Clin Pharmacol*, Aug. 1999, 39, 775–785.

Srinivas, N.R. "Role of Stereoselective Assays in Bioequivalence Studies of Racemic Drugs: Have We Reached a Consensus?" *J Clin Pharmacol*, Feb. 2004, 44, 115–119.

Srinivas, N.R., et al., "Enantiomeric Drug Development: Issues, Considerations, and Regulatory Requirements," *Journal of Pharmaceutical Sciences*, Sep. 2001, 90(9), 1205–1215.

Sarhill, N., et al., "Methylphenidate for fatigue in advanced cancer: a prospective open–lable pilot study," *Am. J. of Hospice & Palliative Care*, 2001, 18(3), 187–192.

Sun, Z. et al., "Methylphenidate is Stereoselectively Hydrolzyed by Human Carboxylesterase CES1 A1," *The Journal of Pharmacology and Experimental Therapeutics*, Aug. 2004, 310(2), 469–476.

Teo, S. K. et al., "The perinatal and postnatal toxicity of D–methylphenidate and D, L–methylphenidate in rats," *Reproductive Toxicology*, 2002, 16, 353–366.

Thai, D. L., et al., "Comparative Pharmacokinetics and Tissue Distribution of the d–enantiomers of Para–substituted Methylphenidate Analogs," *Drug Metabolism and Disposition*, Jun. 1999, 27(6), 645–650.

Thomson, M. R. et al., "Enantioselective Transesterification of Methylphenidate to Ethylphenidate After Coadministration with Ethanol," *Thirty–First Annual ACCP Meeting Abstracts*, Abstract No. 80, 2002.

Volkow, N. D. et al., "Mechanism of action of methylphenidate: Insights from PET imaging studies," *Journal of Attention Disorders*, 2002, 9(Suppl. Jan. 2002), S–31 –S43.

Volkow, N.D. et al., "Effects of Methylphenidate on Regional Brain Glucose Metabolism in Humans: Relationship to Dopamine $D_2$ Receptors," *Am J Psychiatry*, Jan. 1997, 154(1), 50–55.

Volkow, N.D. et al., "Evidence That Methylphenidate Enhances the Saliency of a Mathematical Task by Increasing Dopamine in the Human Brain," *Am J Psychiatry*, Jul. 2004, 161(7), 1173–1180.

Volkow, N. D. et al., "Temporal relationships between the pharmacokinetics of methylphenidate in the human brain and its behavioral and cardiovascular effects," *Psychopharmacology*, 1996, 123, 26–33.

\* cited by examiner

METHODS FOR TREATMENT OF COGNITIVE AND MENOPAUSAL DISORDERS WITH D-THREO METHYLPHENIDATE

CROSS REFERENCE TO RELATED APPLICATIONS

This application is a continuation of 09/903,803, filed Jul. 12, 2001, now U.S. Pat. No. 6,486,177.

FIELD OF THE INVENTION

In one aspect, the present invention is directed to methods for treating fatigue, neurobehavioral slowing and other cognitive disorders and defects due to cancers and treatments associated with cancers, and similar conditions. In a further aspect, the present invention is directed to methods for treating disorders related to menopause, including executive function defects. The methods involve the administration of a composition comprising D-threo methylphenidate that is substantially free of L-threo methylphenidate and of erythro forms of methylphenidate.

BACKGROUND OF THE INVENTION

Advanced cancer typically produces severe pain in patients. This pain is often controlled by the administration of large doses of analgesics, including opioid analgesics. However, the pain relief is often accompanied by undesirable side-effects such as unacceptable sedation and/or a decrease in cognitive function. These side effects have a significant negative impact on the quality of life of the patient. In addition, cancer patients often display one or more of a decrease in cognitive function, fatigue, and neurobehavioral slowing that is unrelated to the administration of analgesics, but may be related to the underlying cancer, the treatment of the cancer, or both.

Menopause is accompanied by several side effects, including an executive function defect. For example, many menopausal women report impairment in short term memory, inability to screen distractions and sustain attention in organization of thoughts and tasks. In addition, women diagnosed with ADD prior to menopause report exacerbation of ADD symptoms during the protracted perimenopausal period and thereafter. See Brown, T. E., Attention-Deficit Disorders and Comorbidities in Children, Adolescents and Aduts, American Psychiatric Press, Washington, D.C., 2000, at p. 40–41.

Methylphenidate has been used to treat nervous system disorders including Attention Deficit Disorder (ADD), a commonly diagnosed nervous system illness in children, Attention Deficit Hyperactivity Disorder (ADHD), and cognitive decline in patients with Acquired Immunodeficiency Syndrome (AIDS) or AIDS related conditions. See, e.g., Brown, G., Intl. J. Psych. Med. 25(1): 21–37 (1995); Holmes et al., J. Clin. Psychiatry 50: 5–8 (1989). The racemic form of methylphenidate also has been proposed to improve cognitive function in patients receiving large doses of medication. See, for example, Bruera et al., Pain (1992) 163–166, Yee et al., Journal of Pain and Symptom Management (1994), Vol. 9, No.2, 122–125, and Meyers et al., Journal of Clinical Oncology (1998) Vol. 16, No. 7, 2522–2527.

Methylphenidate exists as four separate optical isomers as follows:

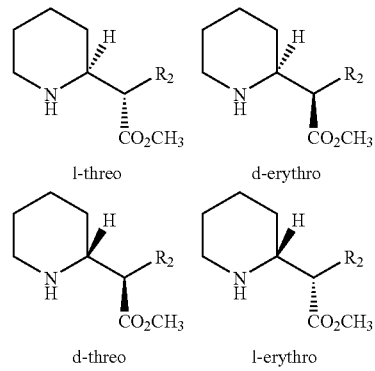

wherein $R_2$ is phenyl. Pharmaceutically acceptable salts are generally administered clinically. Other phenidate drugs, which also can be administered according to the invention, include those in which the methyl group in the above structures is replaced by $C_{2-4}$ alkyl and those in which $R_2$ is optionally substituted with $C_{1-4}$ alkyl.

Clinically, the threo pair of enantiomers of methylphenidate hydrochloride is generally administered for the treatment of ADD and ADHD. The hydrochloride salt is commonly referred to simply as "methylphenidate". Unless indicated otherwise, the term "methylphenidate" is used broadly herein to include methylphenidate and pharmaceutically acceptable salts thereof, including methylphenidate hydrochloride.

The threo racemate (pair of enantiomers) of methylphenidate is a mild central nervous system stimulant with pharmacological activity qualitatively similar to that of amphetamines. Undesirable side effects associated with the use of the DL-threo racemate of methylphenidate include anorexia, weight loss, insomnia, dizziness and dysphoria. Furthermore, the racemate, which is a Schedule II controlled substance, produces a euphoric effect when administered intravenously or through inhalation or ingestion, and thus carries a high potential for abuse.

Srinivas et al. studied the administration of DL-threo-, D-threo, and L-threo-methylphenidate to children suffering from ADHD, and reported that the pharmacodynamic activity of DL-threo-methylphenidate resides in the D-threo isomer (Clin. Pharmacol. Ther., 52: 561–568 (1992)). While DL-threo-methylphenidate is generally used therapeutically, this racemate includes the L isomer which apparently makes no significant contribution to the pharmacological effectiveness of the drug. The removal of the L isomer is expensive, however, and there has been no reason to do so.

It has been discovered that the use of the D-threo isomer (2R:2'R) of methylphenidate, substantially free of the l-threo isomer, produces a methylphenidate medication which retains high activity levels and simultaneously may possess reduced euphoric effect and reduced potential for abuse among patients. See U.S. Pat. Ser. No. 5,908,850, incorporated herein by reference in its entirety. Thus, D-threo-methylphenidate (2R:2'R) may possesses enhanced therapeutic activity with reduced side effects, and 1-threo-methylphenidate may produce undesirable side effects, euphoria and drug abuse potential in patients.

There remains a need for improved methods for alleviating the undesirable symptoms and side-effects described above. This invention is directed to these, as well as other, important ends.

SUMMARY OF THE INVENTION

In one aspect, the present invention provides methods for treating fatigue, neurobehavioral slowing and cognitive side effects arising from cancer, or from a treatment therefor, such as chemotherapy, radiation therapy and administration of medication to control pain. In further aspects, the invention provides methods for alleviation of depression caused by cognitive dysfunction (a "cognitive side effect") and fatigue associated with cancer, and treatments therefor. The methods of the invention involve the administration of D-threo-methylphenidate or a pharmaceutically acceptable salt thereof, substantially free of both L-threo-methylphenidate and erythro methylphenidates.

In some embodiments of the invention, methods are provided for alleviating fatigue and/or neurobehavioral slowing arising from an oncological condition, said method comprising the steps of identifying a patient suffering from said fatigue or neurobehavioral slowing, and administering to said patient a therapeutically effective amount of D-threo-methylphenidate (2R:2'R) or a pharmaceutically acceptable salt thereof, substantially free of the 1-threo isomer.

In further aspects, the present invention provides methods for alleviating fatigue or neurobehavioral slowing arising from the administration of a treatment for an oncological condition, said method comprising the steps of identifying a patient suffering from said fatigue or neurobehavioral slowing, and administering to said patient a therapeutically effective amount of D-threo-methylphenidate (2R:2'R) or a pharmaceutically acceptable salt thereof, substantially free of the 1-threo isomer.

Also provided in accordance with the present invention are methods for alleviating a cognitive side effect of a treatment for an oncological condition, comprising the steps of identifying a patient suffering from a cognitive side-effect of a treatment for an oncological condition; and administering to said patient a therapeutically effective amount of D-threo-methylphenidate (2R:2R) or a pharmaceutically acceptable salt thereof, substantially free of the 1-threo isomer.

In some embodiments of the methods of the invention, the treatment for the oncological condition is the administration of pain management and biological therapies, including pain relief medication, chemotherapy, radiation therapy, and surgery. In some particularly preferred embodiments, the treatment for the oncological condition is chemotherapy or the administration of pain relief medication. In further embodiments of the foregoing methods, the pain relief medication is one or more opioid analgesics, nerve blocks or other psychotropic agents.

In further embodiments of the foregoing methods, the oncological condition is a cancer selected from the group consisting of all malginant conditions, inclduing both solid tumors and nonsolid tumors. In some preferred embodiments, the oncological condition is a solid tumor.

In some embodiments of the foregoing methods, the cognitive side effect is sedation, decreased cognitive function, major depressive disorder, or neurobehavioral slowing. In some preferred embodiments, the cognitive side effect is sedation or decreased cognitive function.

In further aspects, the present invention provides methods for treating a symptom of menopause comprising the steps of identifying a patient suffering from a symptom of menpoause; and administering to said patient a therapeutically effective amount of D-threo-methylphenidate (2R:2'R) or a pharmaceutically acceptable salt thereof, substantially free of the 1-threo isomer.

In some embodiments of the foregoing methods, the symptom of menopause is impairment in short term memory, decreased cognitive function, mental depression, vasomotor instability, nervousness, excitability, fatigue, neurobehavioral slowing, and/or apathy.

In some preferred embodiments of the foregoing methods, the administration of the D-threo-methylphenidate (2R:2'R), or the pharmaceutically acceptable salt thereof, gives rise to efficacious treatment without interfering with patient sleep patterns or engendering anoretic behavior.

DETAILED DESCRIPTION

The methods of the invention involve the administration of D-threo-methylphenidate or a pharmaceutically acceptable salt thereof, substantially free of both L-threo-methylphenidate and erythro methylphenidates. It is now believed that the L isomer may contribute to the side effects associated with the commercial drug, and that it is thus desirable to administer only the active D-threo form of the drug.

Thus, in some embodiments of the invention, methods are provided for alleviating fatigue or neurobehavioral slowing arising from an oncological condition, said method comprising the steps of identifying a patient suffering from said fatigue or neurobehavioral slowing, and administering to said patient a therapeutically effective amount of D-threo-methylphenidate (2R:2'R) or a pharmaceutically acceptable salt thereof, substantially free of the 1-threo isomer.

In further aspects, the present invention provides methods for alleviating fatigue or neurobehavioral slowing arising from the administration of a treatment for an oncological condition, said method comprising the steps of identifying a patient suffering from said fatigue or neurobehavioral slowing, and administering to said patient a therapeutically effective amount of D-threo-methylphenidate (2R:2'R) or a pharmaceutically acceptable salt thereof, substantially free of the 1-threo isomer.

Also provided in accordance with the present invention are methods for alleviating a cognitive side effect (e.g., neurobehavioral slowing) of a treatment for an oncological condition, comprising the steps of identifying a patient suffering from a cognitive side-effect of a treatment for an oncological condition; and administering to said patient a therapeutically effective amount of D-threo-methylphenidate (2R:2'R) or a pharmaceutically acceptable salt thereof, substantially free of the 1-threo isomer.

In some embodiments of the methods of the invention, the treatment for the oncological condition is the administration of pain management and biological therapies, including pain relief medication, chemotherapy, radiation therapy, and surgery. In some particularly preferred embodiments, the treatment for the oncological condition is chemotherapy or the administration of pain relief medication. In further embodiments of the foregoing methods, the pain relief medication is one or more opioid analgesics, nerve blocks or other psychotropic agents.

In further embodiments of the foregoing methods, the oncological condition is a cancer selected from the group consisting of all malginant conditions, inclduing both solid tumors and nonsolid tumors. In some preferred embodiments, the oncological condition is a solid tumor.

In some embodiments of the foregoing methods, the cognitive side effect is sedation, decreased cognitive function, major depressive disorder, or neurobehavioral slowing. In some preferred embodiments, the cognitive side effect is sedation or decreased cognitive function.

In further aspects, the present invention provides methods for treating a symptom of menopause comprising the steps of identifying a patient suffering from a symptom of menpoause; and administering to said patient a therapeutically effective amount of D-threo-methylphenidate (2R:2'R) or a pharmaceutically acceptable salt thereof, substantially free of the 1-threo isomer.

In some embodiments of the foregoing methods, the symptom of menopause is impairment in short term memory, decreased cognitive function, mental depression, vasomotor instability, nervousness, excitability, fatigue, neurobehavioral slowing and/or apathy.

In some preferred embodiments of the foregoing methods, the administration of the D-threo-methylphenidate (2R:2'R), or the pharmaceutically acceptable salt thereof, gives rise to efficacious treatment without interfering with patient sleep patterns or engendering anoretic behavior.

The administration of the pharmacodynamically active D-threo form of methylphenidate may provide efficacious treatment for an entire day with minimal undesirable side effects such as interference with patient sleep patterns or anoretic behavior. It has been surprisingly and unexpectedly discovered that the beneficial effects of the D-threo isomer persist for a longer period time when the D-threo isomer is administered alone than when it is administered in combination with the L-threo isomer.

While it is not intended that the present invention be bound by any particular theory, it is believed that the L isomer functions as an antagonist to the D isomer. Thus, another aspect of the present invention provides methods for ameliorating or counteracting the effects of methylphenidate drugs, comprising administering L-threo methylphenidate to a patient who has a serum level of D-threo methylphenidate.

The present inventors have observed that in the context of ADD, D-threo methylphenidate has a longer duration of action than DL-methylphenidate of at least six hours. Patients who were given the D-threo isomer free of the L isomer performed better in objective tests than patients who received the DL-threo racemate or a placebo, at the 6 hour time point. In contrast, the patients who received DL-threo racemate did not perform better after that time period than those who received a placebo. Furthermore, subjective observations of the same patients indicated that those who received only the D-threo isomer experienced beneficial effects of the drug for longer times than did those who received the DL-threo racemate.

It is expected that D-threo methylphenidate will be particularly useful in treating patients affected by fatigue, neurobehavioral slowing, and other cognitive defects ('cognitive side effects') that are due to cancer, and that are exacerbated by the administration of treatments for cancer such as chemotherapy, radiation therapy, bone marrow transplants, stem cell transplants and administration of medication to control pain. Examples of such cognitive defects include but are not limited to neurobehavioral slowing, sedation, diminished executive function, decreased cognitive function, major depressive disorder and impaired quality of life.

As used herein, the term "oncological condition" is intended to mean all malignant conditions, including all cancers, for example solid tumors and nonsolid tumors. Examples of "oncological conditions" include cancers of the skin, mouth, brain and other nervous tissue, bone, lung, colon and rectum, pancreas, prostate, urinary tract, leukemias and lymphomas.

As used herein, the term "arising from the administration of a treatment for an oncological condition" is intended to mean that the indicated symptom or condition is in whole or in part caused by (i.e., is a side-effect of) the administration of a therapeutic agent used for the treatment of cancer, or for the management of a symptom of the cancer. Examples of agents used for the treatment of cancer include chemotherapeutic agents, including both chemical and radiotherapeutics, and radiation. Examples of agents used for the management of a symptom of the cancer include pain relief medications such as opioid or opoid-like analgesics and non-steroidal anti-inflammatory agents.

As used herein, the term "alleviating a cognitive side effect of a treatment for an oncological condition" means the lessening of the severity of a cognitive side effect caused in whole or in part by the administration of a treatment for an oncological condition. The term "cognitive side effect" as used herein denotes an impairment of one or more cognitive functions that results in whole or in part from the administration of an agent used for the treatment of cancer. Examples of cognitive side effects include sedation, neurobehavioral slowing, decreased cognitive function, depression, apathy, decreased libido and derpersonalization. The term "decreased cognitive function" is intended to mean a decrease in any or all aspects of thought, attention, perception, and/or memory.

As used herein, the term "menopause" is given its normal meaning of the period during which marks the permanent cessation of menstrual activity. The term "symptom of menopause" in intended to include those symptoms associated with menopause, including vasomotor instability, nervousness, excitability, fatigue, neurobehavioral slowing, apathy, mental depression and impairment of short term memory. As used herein, the term "executive function defect" is intended to include but is not limited to one or more defects in the cognitive mechanisms responsible for focusing attention, goal-related behavior, strategic planning and problem solving.

The methods of the invention will find use with patients, including outpatients, with all types of cancer, either primary or metastatic.

According to one method of the present invention, dosage forms are administered of D-threo methylphenidate substantially free of L-threo methylphenidate and of erythro methylphenidates. "Substantially free", as used herein, means that the dosage forms comprise at least about 95 percent, preferably at least about 97 percent, and more preferably at least about 99 percent of the D-threo isomer, to the exclusion of the L-threo and erythro forms. The D-threo form can be isolated by methods known to those skilled in the art.

In accordance with the present invention, the D-threo methylphenidate can be administered in any of a variety of dosage regimes. Such regimes include chronic single, bolus dosages, i.e., where one dose being administered in a predetermined time period, for example twenty four hours. Further dosage regimes include those where multiple dosages are manually administered, and dosage forms where a single dosage form is administered that effectively mimics multiple dosages, such as pulsatile release dosage forms. Further dosage forms useful with the present invention include delay release and extended release (i.e., "time release") dosage forms. The selection of appropriate dosage forms for an individual patient will depend upon the individual circumstances, and will be apparent to those of skill in the art.

"Chronic", as used herein, refers to continuous, regular, long-term therapeutic administration, i.e. periodic administration without substantial interruption, such as, for example, daily, for a time period of at least several weeks or months to several years, for the purpose of treating a patient needing treatment.

"Bolus", as used herein, refers to administration of a drug as a single event. The term "bolus" is intended to exclude dosage forms such as sustained release, pulsed release, and time release, and includes any dosage form which can be used to deliver a single dose. According to the present invention, a bolus is preferably administered to a patient in need of treatment once daily, more preferably in the morning. The bolus dosages of the present invention may be adminstered in any conventional form known to those skilled in the art. Suitable methods for administration include oral dosage forms, injection, and infusion.

For pharmaceutical use, the D-threo methylphenidate substantially free of L-threo methylphenidate and of erythro methylphenidates as described herein can be taken up in pharmaceutically acceptable carriers, such as, for example, solutions, suspensions, tablets, capsules, ointments, elixirs and injectable compositions. Pharmaceutical preparations generally can contain from about 1% to about 90% by weight of active ingredient. Preparations which are in single dose form, "unit dosage form", preferably contain from about 20% to about 90% active ingredient. As used herein, the term "active ingredient" refers to D-threo methylphenidate substantially free of L-threo methylphenidate and of erythro methylphenidates as described herein, salts thereof, and mixtures of D-threo methylphenidate as described herein with other pharmaceutically active compounds. Dosage unit forms such as, for example, tablets or capsules, typically contain from about 0.001 to about 1.0 g of active ingredient. Pharmaceutical preparations may be administered orally, parenterally, or topically. Pharmaceutical preparations containing compounds described herein may be prepared by methods known to those skilled in the art, such as, for example, conventional mixing, granulating, dissolving, or lyophilizing. Oral dosage forms include capsules, pills, tablets, troches, lozenges, melts, powders, solutions, suspensions and emulsions. The oral dosage forms provided by the invention can be in the form of tablets, caplets, and the like and can be of any shape suitable for oral administration of a drug, such as spheroidal, cube-shaped, oval, bean shaped, or ellipsoidal. For oral dosage forms, for example, the compounds may be combined with one or more solid pharmaceutically acceptable carriers, optionally granulating the resulting mixture. Pharmaceutically acceptable adjuvants may optionally be included, such as, for example, flow-regulating agents and lubricants. Suitable carriers include, for example, fillers such as sugars, cellulose preparations, calcium phosphates; and binders such as methylcellulose, hydroxymethylcellulose, and starches, such as, for example, maize starch, potato starch, rice starch, and wheat starch. The dosage form may be in the form of granules, which may be irregularly shaped. The dosage form can comprise a capsule containing particles. Examples of orally administrable pharmaceutical preparations are dry-filled capsules consisting of gelatin, and soft sealed capsules consisting of gelatin and a plasticizer such as glycerol or sorbitol. The dry-filled capsules may contain the active ingredient in the form of a granulate, for example in admixture with fillers, binders, glidants, and stabilizers. In soft capsules, the active ingredient is preferably dissolved or suspended in a suitable liquid adjuvant, such as, for example, a fatty oil, paraffin oil, or liquid polyethylene glycol, optionally in the presence of stabilizers. Other oral administrable forms include syrups containing active ingredient, for example, in suspended form at a concentration of from about 0.01% to 20%, or in a similar concentration that provides a suitable single dose when administered, for example, in measures of from about 2 to about 5 milliliters. Suitable excipients for use in oral liquid dosage forms include diluents such as water and alcohols, for example ethanol, benzyl alcohol and polyethylene alcohols, either with or without the addition of a pharmaceutically acceptable surfactant, suspending agent, or emulsifying agent. Also suitable are powdered or liquid concentrates for combining with liquids such as milk. Such concentrates may also be packed in single dose quantities.

In accordance with the present invention, D-threo methylphenidate as described herein may be administered parenterally, that is, subcutaneously, intravenously, intramuscularly, or interperitoneally, as injectable dosages of the compound in a physiologically acceptable diluent with a pharmaceutical carrier. Solutions for parenteral administration may be in the form of infusion solutions. A pharmaceutical carrier may be, for example, a sterile liquid or mixture of liquids such as water, saline, aqueous dextrose and related sugar solutions, an alcohol such as as ethanol, glycols such as propylene glycol or polyethylene glycol, glycerol ketals such as 2,2-dimethyl-1,3-dioxolane-4-methanol, ethers such as poly(ethyleneglycol)400, oils, fatty acids, fatty acid esters or glycerides, with or without the addition of a pharmaceutically acceptable surfactant such as a soap or detergent, suspending agent such as pectin, carbomers, methylcellulose, hydroxypropylmethylcellulose, or carboxymethylcellulose, or emulsifying agent or other pharmaceutically acceptable adjuvants. Examples of oils which may be used in parenteral formulations include petroleum, animal, vegetable, or synthetic oils such as, for example, peanut oil, soybean oil, sesame oil, cottonseed oil, corn oil, olive oil, petrolatum, and mineral oil. Suitable fatty acids include, for example, oleic acid, stearic acid, and isostearic acid. Suitable fatty acid esters include ethyl oleate and isopropyl myristate. Suitable soaps include alkaline metal, ammonium and triethanolamine salts of fatty acids. Suitable detergents include cationic detergents such as dimethyl dialkyl ammonium halides and alkyl pyridinium halides; anionic detergents such as alkyl, aryl and olefin sulfonates, monoglyceride sulfates and sulfosuccinates; nonionic detergents such as fatty amino oxides, fatty acid alkanolamides and polyoxyethylenepropylene copolymers; and amphoteric detergents such as alkyl-(-aminopropionates and 2-alkylimidazoline quaternary ammonium salts; as well as mixtures of detergents. Parenteral preparations will typically contain at least about 0.01% by weight of active ingredient in solution. Preservatives and buffers may also be used advantageously. Injection suspensions may include viscosity-increasing substances such as, for example, sodium carboxymethylcellulose, sorbitol or dextran, and may also include stabilizers. In order to minimize irritation at the site of injection, injectable compositions may contain a non-ionic surfactant having a hydrophile-lipophile balance (HLB) of from about 12 to about 17. The quantity of surfactant in such formulations ranges from about 5% to about 15% by weight. The surfactant may be a single component having the above HLB or a mixture of two or more components having the desired HLB. Particular examples of useful surfactants include polyethylene sorbitan fatty acid esters, such as, for example, sorbitan monooleate.

In addition to parenteral administration, D-threo methylphenidate as described herein can be-formulated for nasal administration, particularly in the form of powders, nasal drops, or aerosols. The compounds of the invention also can be administered dermally, via, for example, trans-dermal patches.

The preferred quantity of D-threo methylphenidate to be used in a dosage for treating a particular patient can be readily determined by one skilled in the art. Factors determining the appropriate dosage include the weight and age of the patient, the type and extent of the disorder being treated, and other conditions of the patient including other disorders and other medications, if any, that the patient is taking. Generally, the dosage of D-threo methylphenidate will be from about 0.01 mg/kg of patient body weight to about 1 mg/kg of patient body weight. Appropriate quantities can be determined by one skilled in the art. For example, a relatively small child will generally require a dose of from about 0.03 to about 0.3 mg/kg, while a larger child or an adult may require a dose of from about 0.1 mg/kg to about 0.4 or 0.5 mg/kg.

A physician treating a patient with cancer will generally titrate the dose of methylphenidate until the desired therapeutic effects is achieved. For example, a patient with cancer receiving an opioid analgesic for pain management will initially be administered a minimum dose of 2.5 mg of d-MPH b.i.d. at the time of the opioid analgesic, with dose increasing a clinically warranted.

Response by patients with cognitive deficiencies described herein is generally determined by two types of measurements: objective measures of a patient's ability to concentrate and remain focused on a task such as performing a math test; and subjective scores of a patient's performance.

The following examples are merely illustrative of the present invention and should not be considered limiting of the scope of the invention in any way. These examples and equivalents thereof will become more apparent to those skilled in the art in light of the present disclosure and the accompanying claims.

EXAMPLES

Determination of Symptoms

Patients can be evaluated for cognitive impairment by any of the tests known in the art. For example, High Sensitivity Cognitive Screen (HSCS) can test six cognitive domains: memory, language, visual-motor, spatial, attention/concentration, and self-regulation and planning (see, for example, Faust D. and Fogel B. S.: The development and initial validation of a sensitive bedside cognitive screening test. J. Nerv. Ment. Dis.; 177:25–31, 1989).

Global cognitive function can be evaluated by the Mini-Mental State Exam (MMSE; see, for example, Folstein M. F., Folstin S. E., McHugh P. R.: "Minimental State": a practical method for grading the cognitive state of patients for the clinician. J. Psychiatry Res. 12:189–198, 1975) Attention and concentration can be evaluated via the Trial Making Test-Part A (See, for example, Reitan, R. M.: Validity of the Trail Making Test as an indicator of organic brain damage. Perceptual Motor Skills 8:271–276, 1958), and the Digit Span, Forward and Backward test (see, for example, Wechsler D. Wechsler Adult Intelligence Scale-Revised Manual. New York; Psychological Corporation, 1981)).

Visuospatial skills can be evaluated by, for example, the Revised-Rey Osterrieth Complex Figure test, (see, for example, Osterrieth R. A. Le test de copie d'une fugure complexe. Archives de Psychologie, 1944, 30, 206–356). Impairment to language functions can be evaluated by, for example, the Verbal Fluency (F-A-S) test (see for example Kaplan, E. F., Goodglass, H., Weintraub, S. The Boston Naming Test. Boston: E. Kaplan & H. Goodglass, 1978).

Learning impairment can be evaluated by, for example, the California Verbal Learning Test (see, for example, Delis, D. C., Kramer, J. H., Kaplan, E., Ober, B. A. California Verbal Learning Test-Research Edition. The Psychological Corp., New York, 1987).

Memory impairment can be evaluated by, for example, the Revised-Rey Osterrieth Complex Figure, Immediate Recall test and/or the Revised-Rey Osterrieth Complex Figure, Delayed Recall test, (see, for example, Osterrieth R A, above); the California Verbal Learning Test, Immediate Recall, and/or the California Verbal Learning Test, Delayed Recall, the California Verbal Learning Test, Recognition (See, for example, Delis et al., above).

Executive function impairment can be evaluated by, for example, the Trail Making Test-Part B (See, for example, Reitan et al., above).

Quality of Life can be evaluated by the FACIT-F tests (Fatigue Scale), the FACT-F test (Functional Assessment of Cancer Therapy—Fatigue Scale), the FACT-G test (Functional Assessment of Cancer Therapy—General Scale), and the FACT-BR test (Functional Assessment of Cancer Therapy—Brain Subscale), (see, for example Cella, D. F., Tulsky, D. S., Gray, G., Sarafian, B., Linn E. Bonomi, A., et al.: The functional assessment of cancer therapy scale: development and validation of the general measure. J. Clin. Oncol. 11:570–579, 1993; Weitzner, M. A., Meyers, C. A., Gelke, C. K., Byrne, K. S., Cella, D. F., Levin, V. A.: The Functional Assessment of Cancer Therapy (FACT) scale: Development of a brain subscale and revalidation of the general version (FACT-G) in patients with primary brain tumors. Cancer 75:1151–1161, 1995; and Yellin, S. B., Cella, D. F., Webster, K., Blendowsky, C., Kaplan, E.,: Measuring fatigue and other anemia-related symptoms with the Functional Assessment of Cancer Therapy (FACT) Measurement System., J. Pain Symptom Manage. 13:63–74, 1997). Each of the foregoing publications are incorporated herein by reference in their entirety.

Depression can be evaluated by, for example, the Center for Epidemiologic Studies Depression (CES-D) Scale (see, for example, Radloff, L. S.: The CES-D scale: A self-report depression scale for research in the general population. Applied Psychological Measurement 1:385–401, 1977), or by Beck Depression Inventory (BDI) (see, for example, Beck, A. T. and Beamesderfer, A: Assessment of depression: the Depression Inventory. Mod. Probl. Pharmacopsychiatry; 7:155–169, 1974).

Example 1

Administration of D-threo-methylphenidate Hydrochloride (d-MPH) in the Treatment of Cognitive Dysfunction Related to Chemotherapy in Adult Cancer Patients Patients that have received at least one cycle of cytotoxic chemotherapy, preferably within 2 months prior to treatment, and who display one or more symptoms of cognitive dysfunction are evaluated as candidates for d-MPH treatment. Prior to commencement of treatment, patients are evaluated for the following: medical history/concomitant illnesses, physical examination, 12-lead electrocardiogram, routine laboratory tests and assessments of cognitive function. Tests for cognitive function can include those know to those of skill in the art, for example those described above. Patients having no medical contraindication to the use of methylphenidate are then initially administered d-MPH 5 mg/day (2.5 mg b.i.d given 4 to 6 hours apart). The dose may be increased as clinically warranted if there are no adverse effects that preclude dose-escalation and there is no significant therapeutic response.

Daily doses can be administered two or three times per day. The maximum dose will be 50 mg/day, given two to three times per day.

Patients are evaluated periodically for one or more of fatigue, neurobehavioral slowing, sedation, decreased cognitive function, and major depressive disorder. Patients receiving the foregoing treatment will display an alleviation of one or more of the foregoing symptoms.

Example 2

Administration of D-threo-methylphenidate Hydrochloride (d-MPH) in the Treatment of Menopausal Women Menopausal women who display one or more symptoms including an executive function defect, decreased cognitive function, mental depression, vasomotor instability, nervousness, excitability, fatigue, neurobehavioral slowing, apathy, or impairment of short term memory are evaluated as candidates for d-MPH treatment. Prior to commencement of treatment, patients are evaluated for the following: medical history/concomitant illnesses, physical examination, 12-lead electrocardiogram, routine laboratory tests and assessments of the severity of the symptom.

Patients having no medical contraindication to the use of methylphenidate are then initially administered d-MPH 5 mg/day (2.5 mg b.i.d given 4 to 6 hours apart). The dose may be increased as clinically warranted if there are no adverse effects that preclude dose-escalation and there is no significant therapeutic response. Daily doses can be administered two or three times per day. The maximum dose will be 50 mg/day, given two to three times per day. Once a patient's optimal dose has been determined, the patient will remain on this dose for at least 2 weeks.

Patients are evaluated for one or more of executive function defect, decreased cognitive function, mental depression, vasomotor instability, nervousness, excitability, fatigue, neurobehavioral slowing, apathy, or impairment of short term memory. Patients receiving the foregoing treatment will display an alleviation of one or more of the foregoing symptoms.

Example 3

Administration of D-threo-methylphenidate hydrochloride (d-MPH) in the Treatment of Menopausal Women Having Previously Diagnosed Attention Deficit Disorder (ADD)

Menopausal women who have been previously been diagnosed with Attention Deficit Disorder ("ADD") and who are suspected having exacerbated ADD symptoms are evaluated for one or more symptoms of ADD according to previously published methods (for example, see American Psychiatric Association. Diagnostic and Statistical Manual of Mental Disorders, Fourth Edition (DSM-IV). Washington, D.C., 1994, pp 78–85).

Patients having no medical contraindication to the use of methylphenidate are then initially administered d-MPH 5 mg/day (2.5 mg b.i.d given 4 to 6 hours apart). The dose may be increased as clinically warranted if there are no adverse effects that preclude dose-escalation and there is no significant therapeutic response. Daily doses can be administered two or three times per day. The maximum dose will generally be approximately 50 mg/day, given two to three times per day.

Patients are periodically evaluated for efficacy of treatment. Patients receiving the foregoing treatment will display an alleviation of one or more of the foregoing symptoms.

It is intended that each of the patents, applications, and printed publications mentioned or referred to in this specification be hereby incorporated by reference in their entirety.

As those skilled in the art will appreciate, numerous changes and modifications may be made to the preferred embodiments of the invention without departing from the spirit of the invention. It is intended that all such variations fall within the scope of the invention.

What is claimed is:

1. A method for alleviating fatigue arising from an oncological condition, said method comprising the steps of:
   identifying a patient suffering from said fatigue, and
   administering to said patient a unit dosage comprising a compound having the formula

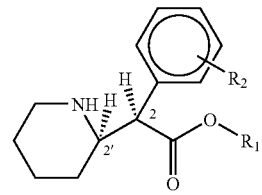

or a pharmaceutically acceptable salt thereof, wherein $R_1$ is $C_1$–$C_4$ alkyl, and $R_2$ is hydrogen or $C_1$–$C_4$ alkyl, in a pharmaceutically acceptable carrier or diluent, said dosage having less than 10% by weight of other stereoisomers of the compound or salt.

2. The method of claim 1 wherein the unit dosage is 1% to about 90% by weight of active ingredient.

3. The method of claim 1 wherein the unit dosage is 20% to about 90% by weight of active ingredient.

4. The method of claim 1 wherein the unit dosage is in a form suitable for oral administration.

5. The method of claim 1 wherein said oncological condition is a cancer selected from the group consisting of solid tumors and nonsolid tumors.

6. The method of claim 1 wherein said oncological condition is a solid tumor.

7. A method for alleviating fatigue arising from the administration of a treatment for an oncological condition, said method comprising the steps of:
   identifying a patient suffering from said fatigue, and
   administering to said patient a unit dosage comprising a compound having the formula

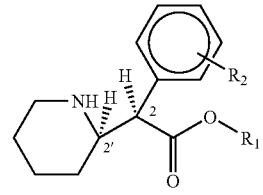

or a pharmaceutically acceptable salt thereof, wherein $R_1$ is $C_1$–$C_4$ alkyl, and $R_2$ is hydrogen or $C_1$–$C_4$ alkyl, in a pharmaceutically acceptable carrier or diluent, said dosage having less than 10% by weight of other stereoisomers of the compound or salt.

8. The method of claim 7 wherein the unit dosage is 1% to about 90% by weight of active ingredient.

9. The method of claim 7 wherein the unit dosage is 20% to about 90% by weight of active ingredient.

10. The method of claim 7 wherein the unit dosage is in a form suitable for oral administration.

11. The method of claim 7 wherein said treatment for said oncological condition is chemotherapy or radiation therapy.

12. The method of claim 7 wherein said treatment for said oncological condition is chemotherapy.

13. A method for alleviating neurobehavioral slowing arising from an oncological condition, said method comprising the steps of:
   identifying a patient suffering from said neurobehavioral slowing, and
   administering to said patient a unit dosage comprising a compound having the formula

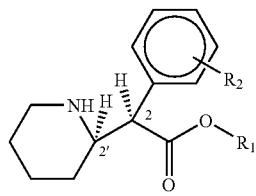

or a pharmaceutically acceptable salt thereof, wherein $R_1$ is $C_1$–$C_4$ alkyl, and $R_2$ is hydrogen or $C_1$–$C_4$ alkyl, in a pharmaceutically acceptable carrier or diluent, said dosage having less than 10% by weight of other stereoisomers of the compound or salt.

14. The method of claim 13 wherein the unit dosage is 1% to about 90% by weight of active ingredient.

15. The method of claim 13 wherein the unit dosage is 20% to about 90% by weight of active ingredient.

16. The method of claim 13 wherein the unit dosage is in a form suitable for oral administration.

17. The method of claim 13 wherein said oncological condition is a cancer selected from the group consisting of solid tumors and nonsolid tumors.

18. The method of claim 13 wherein said oncological condition is a solid tumor.

19. A method for alleviating neurobehavioral slowing arising from the administration of a treatment for an oncological condition, said method comprising the steps of:
   identifying a patient suffering from said neurobehavioral slowing, and
   administering to said patient a unit dosage comprising a compound having the formula

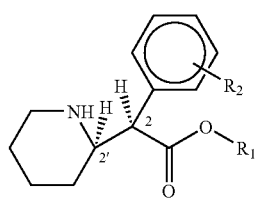

or a pharmaceutically acceptable salt thereof, wherein $R_1$ is $C_1$–$C_4$ alkyl, and $R_2$ is hydrogen or $C_1$–$C_4$ alkyl, in a pharmaceutically acceptable carrier or diluent, said dosage having less than 10% by weight of other stereoisomers of the compound or salt.

20. The method of claim 19 wherein the unit dosage is 1% to about 90% by weight of active ingredient.

21. The method of claim 19 wherein the unit dosage is 20% to about 90% by weight of active ingredient.

22. The method of claim 19 wherein the unit dosage is in a form suitable for oral administration.

23. The method of claim 19 wherein said treatment for said oncological condition is chemotherapy or radiation therapy.

24. The method of claim 19 wherein said treatment for said oncological condition is chemotherapy.

25. The method of claim 19 wherein said oncological condition is a cancer selected from the group consisting of solid tumors and nonsolid tumors.

26. The method of claim 19 wherein said oncological condition is a solid tumor.

27. A method for alleviating a cognitive side effect of a treatment for an oncological condition, comprising the steps of:
   identifing a patient suffering from a cognitive side-effect of a treatment for an oncological condition; and
   administering to said patient a unit dosage comprising a compound having the formula

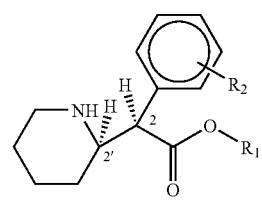

or a pharmaceutically acceptable salt thereof, wherein $R_1$ is $C_1$–$C_4$ alkyl, and $R_2$ is hydrogen or $C_1$–$C_4$ alkyl, in a pharmaceutically acceptable carrier or diluent, said dosage having less than 10% by weight of other stereoisomers of the compound or salt.

28. The method of claim 27 wherein the unit dosage is 1% to about 90% by weight of active ingredient.

29. The method of claim 27 wherein the unit dosage is 20% to about 90% by weight of active ingredient.

30. The method of claim 27 wherein the unit dosage is in a form suitable for oral administration.

31. The method of claim 27 wherein said oncological condition is a cancer selected from the group consisting of solid tumors and nonsolid tumors.

32. The method of claim 27 wherein said oncological condition is a solid tumor.

33. The method of claim 27 wherein said treatment for said oncological condition is the administration of pain relief medication, chemotherapy, radiation therapy, or surgery.

34. The method of claim 27 wherein said treatment for said oncological condition is the administration of pain relief medication.

35. The method of claim 34 wherein said pain relief medication is and opioid analgesic.

36. The method of claim 27 wherein said cognitive side effect is sedation, decreased cognitive function, major depressive disorder, or neurobehavioral slowing.

37. The method of claim 36 wherein said cognitive side effect is sedation, decreased cognitive function or neurobehavioral slowing.

38. The method of claim 36 wherein said cognitive side effect is sedation.

39. A method for treating a symptom of menopause comprising the steps of:
   identifing a patient suffering from a symptom of menopause; and
   administering to said patient a unit dosage comprising a compound having the formula

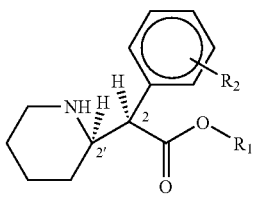

or a pharmaceutically acceptable salt thereof, wherein $R_1$ is $C_1$–$C_4$ alkyl, and $R_2$ is hydrogen or $C_1$–$C_4$ alkyl, in a pharmaceutically acceptable carrier or diluent, said dosage having less than 10% by weight of other stereoisomers of the compound or salt.

40. The method of claim 39 wherein the unit dosage is 1% to about 90% by weight of active ingredient.

41. The method of claim 39 wherein the unit dosage is 20% to about 90% by weight of active ingredient.

42. The method of claim 39 wherein the unit dosage is in a form suitable for oral administration.

43. The method of claim 39 wherein said symptom of menopause is decreased cognitive function.

44. The method of claim 39 wherein said symptom of menopause is vasomotor instability.

45. The method of claim 39 wherein said symptom of menopause is nervousness.

46. The method of claim 39 wherein said symptom of menopause is mental depression.

47. The method of claim 39 wherein said symptom of menopause is excitability.

48. The method of claim 39 wherein said symptom of menopause is fatigue.

49. The method of claim 39 wherein said symptom of menopause is apathy.

50. The method of claim 39 wherein said symptom of menopause is impairment of short term memory.

51. The method of claim 1 wherein said administration of said compound gives rise to efficacious treatment without interfering with patient sleep patterns or engendering anoretic behavior.

52. The method of claim 7 wherein said administration of said compound gives rise to efficacious treatment without interfering with patient sleep pattern or engendering anoretic behavior.

53. The method of claim 13 wherein said administration of said compound gives rise to efficacious treatment without nterfering with patient sleep patterns or engendering anoretic behavior.

54. The method of claim 19 wherein said administration of said compound gives rise to efficacious treatment without interfering with patient sleep patterns or engendering anoretic behavior.

55. The method of claim 27 wherein said administration of said compound gives rise to efficacious treatment without interfering with patient sleep patterns or engendering anoretic behavior.

56. The method of claim 39 wherein said administration of said compound gives rise to efficacious treatment without interfering with patient sleep patterns or engendering anoretic behavior.

\* \* \* \* \*

UNITED STATES PATENT AND TRADEMARK OFFICE
CERTIFICATE OF CORRECTION

PATENT NO. : 7,115,631 B2
APPLICATION NO. : 10/195974
DATED : October 3, 2006
INVENTOR(S) : Jerome B. Zeldis et al.

It is certified that error appears in the above-identified patent and that said Letters Patent is hereby corrected as shown below:

Title Page,
Item (75), Inventors:
Delete "David Sterling," and insert -- David I. Stirling, --.

Title Page, Page 2
Item (56), References Cited, OTHER PUBLICATIONS:
Col. 1 line 11 – "Srinivas, et al.," reference, delete "deficite" and insert -- deficit --.
      line 37 – "Douzenis, et al.," reference, delete "Phychiatric" and insert
        --Psychiatric --.
      line 42 – "Greehill," reference, delete "Greehill," and insert-- Greenhill, --
      line 43 – "Greehill," reference, delete "*Psychoparmacology*," and insert
        -- *Psychopharmacology*, --.
      line 51 – "Klibanov, A.M.," reference, delete "enzyumes" and insert
        -- enzymes--.
Col. 2 line 4 – "Srinivas, et al.," reference, delete " "Anantioselective" and insert
        -- Enantioselective --.
      line 24 – "Bruera, E., et al.," reference, delete "contiuous" and insert
        -- continuous--.
      line 42 – "Meyers, C.A., et al.," reference, delete "*Clincial*" and insert
        -- *Clinical* --.
      line 56 – "Yee, J.D., et al.," reference, delete " "Dextromaphetamine" and insert
        -- "Dextroamphetamine --.
Page 3
Col. 2 line 33 – "Aoyana, T., et al.," reference, delete "Aoyana," and insert
        -- Aoyama,--.
      line 36/37 – "Axten, J.M., et al.," reference, delete "dl-threo-methyphenidate:
        preperation" and insert-- dl-threo-methylphenidate: preparation --.
      line 45 – "Davies. H.M.L., et al.," reference, delete "$C_2$-symetric" and insert
        -- $C_2$-symmetric --.
      line 51 – "Dirksen, S.J.H., et al., reference, delete " "A postmarking clinical" and
        insert -- "A postmarketing clinical --.
      line 60 – "Hubbard, J.W., et al.," reference, delete "deficit-hyperactitiy" and
        insert -- deficit-hyperactivity --.
Page 4
Col. 1 line 10 – "Naito, T., et al.," reference, delete "β-phenyl-2-and" and insert
        -- α-phenyl-2-and --.
      line 40 – "Aoyama, T., et al," reference, delete "encantiomers" and insert
        -- enantiomers --.
      line 63 – "Garland, E. J.," reference, delete "hyperacitivity" and insert
        -- hyperactivity --.

UNITED STATES PATENT AND TRADEMARK OFFICE
CERTIFICATE OF CORRECTION

PATENT NO. : 7,115,631 B2
APPLICATION NO. : 10/195974
DATED : October 3, 2006
INVENTOR(S) : Jerome B. Zeldis et al.

It is certified that error appears in the above-identified patent and that said Letters Patent is hereby corrected as shown below:

Page 4
Col. 2 line 21 – "Lin, J. H., and Lu, A. H.," reference, delete "pharmacolinetics" and insert -- pharmacokinetics --.
line 31 – "McCarthy, M.," reference, delete "ADHA," " and insert -- ADHD," --.
line 32 – "Mehta, M.A., et al.," reference, delete "enchances" and insert -- enhances --.
line 51 – "Swanson, J. M., et al.," reference, delete "ADHA," "and insert -- ADHD," --.

Page 5
Col. 1 line 16 – "Davids, E. et al," reference, delete "hyperacitivity" and insert -- hyperactivity --.
line 23 – "Ding, Y.-D. et al.," reference, delete "Ding, Y.-D. et al.," and insert --Ding, Y.-S. et al., --.
line 44 – "Patrick, K. S. et al.," reference, delete "attention-deficit/hyperacitivity" and insert -- attention-deficit/hyperactivity --.
Col. 2 line 5 – "Rouhi R. I. et al.," reference, delete ""Rouhi, R. I. et al.," and insert -- Rouhi, A. M. et al., --.
line 8 – "Shader R. I. et al," reference, delete "Hyperacitivity" and insert -- Hyperactivity --.
line 22 – "Sun, Z. et al.," reference, delete "Hydrolzyed" and insert -- Hydrolyzed --.

Column 1,
Line 51, delete "Aduts," and insert -- Adults, --.

Column 2,
Line 23, delete "$C_{2-4}$ alkyl" and insert-- $C_2$-$C_4$ alkyl --.
Line 24, delete "$C_{1-4}$ alkyl." and insert -- $C_1$-$C_4$ alkyl. --.

Column 3,
Line 38, delete "(2R:2R)" and insert -- (2R:2'R) --.
Line 53, delete "malginant" and insert-- malignant --.
Line 53, delete "inclduing" and insert -- including --.
Lines 63-64, delete "menpoause;" and insert -- menopause; --

Column 4,
Line 60, delete "malginant" and insert -- malignant --.

Column 5,
Lines 3-4, delete "menpoause:" and insert -- menopause: --.

UNITED STATES PATENT AND TRADEMARK OFFICE
CERTIFICATE OF CORRECTION

PATENT NO. : 7,115,631 B2
APPLICATION NO. : 10/195974
DATED : October 3, 2006
INVENTOR(S) : Jerome B. Zeldis et al.

It is certified that error appears in the above-identified patent and that said Letters Patent is hereby corrected as shown below:

Column 6,
Line 9, delete "opoid-like" and insert -- opioid-like --.
Line 21, delete "derpersonalization." and insert -- depersonalization. --.
Line 28, delete "in intended" and insert --is intended --.

Column 8,
Line 20, delete "such as as ethanol," and insert -- such as ethanol, --.
Line 42, delete "amino" and insert -- amine --.
Line 63, delete "be-formulated" and insert -- be formulated --.

Column 10,
Line 61, delete "know" and insert -- known --.

Column 14,
Line 52, delete "and" and insert -- an --.

Signed and Sealed this

Sixteenth Day of January, 2007

JON W. DUDAS
*Director of the United States Patent and Trademark Office*